United States Patent
Ritz et al.

(10) Patent No.: US 6,489,605 B1
(45) Date of Patent: Dec. 3, 2002

(54) DEVICE TO AID THE ORIENTATION OF BLIND AND PARTIALLY SIGHTED PEOPLE

(75) Inventors: Maria Ritz, Berlin (DE); Lutz Konig, Berlin (DE); Ludger Woste, Berlin (DE)

(73) Assignee: Vistac GmbH, Tetlow (DE)

( * ) Notice: Subject to any disclaimer, the term of this patent is extended or adjusted under 35 U.S.C. 154(b) by 0 days.

(21) Appl. No.: 09/496,080

(22) Filed: Feb. 1, 2000

(30) Foreign Application Priority Data

Feb. 2, 1999 (DE) ..................................... 299 02 241 U

(51) Int. Cl.[7] ................................................. A61H 3/00
(52) U.S. Cl. ........................ 250/221; 367/116; 434/112
(58) Field of Search .............................. 250/221, 222.1; 434/112, 116; 367/116

(56) References Cited

U.S. PATENT DOCUMENTS

| | | | |
|---|---|---|---|
| 3,546,467 A | 12/1970 | Benjamin, Jr. et al. | |
| 3,654,477 A | 4/1972 | Benjamin, Jr. | |
| 4,051,365 A | * 9/1977 | Fukuyama et al. | ...... 250/222.1 |
| 4,712,003 A | 12/1987 | Ban et al. | |
| 5,487,669 A | 1/1996 | Kelk | |
| 5,687,136 A | 11/1997 | Borenstein | |
| 6,298,010 B1 | * 10/2001 | Ritz et al. | ................. 367/116 |

FOREIGN PATENT DOCUMENTS

WO PCT/FI97/00491 8/1997
WO 198 20 176 A1 11/1998

* cited by examiner

*Primary Examiner*—Stephone Allen
(74) *Attorney, Agent, or Firm*—Mallinckrodt & Mallinckrodt; Robert R. Mallinckrodt

(57) ABSTRACT

The invention relates to a device to aid the orientation of blind and partially sighted people. The device comprises a long cane and an additional device comprising a laser measuring system. By transmitting and receiving laser beams the laser measuring system detects objects in a planar detection area of a detection plane containing the long cane. Indicating means indicates the presence and the absence of objects in this planar detection area by a first and by a second information, respectively, for example by the presence of a determined signal and by the absence of a determined signal. This allows to detect objects above the long cane.

20 Claims, 3 Drawing Sheets

DEVICE TO AID THE ORIENTATION OF BLIND AND PARTIALLY SIGHTED PEOPLE

BACKGROUND OF THE INVENTION

This invention relates to a device to aid the orientation of blind and partially sighted people.

Blind or partially sighted people usually use a cane (so-called mobility cane or long cane) for orientation, with which objects in a distance up to 1.2 m can be detected. The orientation with such a long cane has several disadvantages. For example, objects cannot be detected if they are not located near the ground and within a distance of about 1.2 m. The head and the breast area of the blind person cannot be protected. Objects in this height are often recognised to late which often result in hurting the blind person.

A number of devices for blind or partially sighted people is known which use contactless distance measurement systems to overcome the disadvantages of the long cane. Different versions of such a contactless distance measurement system are known. These devices comprise a transmitter which sends out a measurement beam and if the beam is reflected by an object a receiver detects the reflected beam. The distance between the device and the object is determined either by time of flight measurement, phase modulation measurement or by triangulation measurement. The measurement beam can be electro-magnetic (IR-radiation or laser beam) or sonic. The determined distance will be converted into a distance-dependent correcting variable which will be supplied to an indicator that displays the distance in a way that is adapted to the needs of the blind and partially sighted persons. Such indicators use either acoustic or tactile signals.

Furthermore, long cane are known, which are provided with an additional device comprising a contactless measuring system by means of which space ranges are detected, which cannot be detected by the long cane itself. The beam lobe of the measuring system is directed in the walking direction and considerably exceeds the range of the long cane. Due to the extended beam lobe (particularly when using ultrasonic devices) such additional devices detects a large space area. When an object is detected in this space area, a warning signal is supplied to the blind person.

SUMMARY OF THE INVENTION

It has been found that known contactless measuring devices, regardless whether they are used in combination with a long cane or not, have disadvantages which make them very uncomfortable in use. The known devices generate warning signals or distance signals for indicating objects which are not located in the range relevant for the blind person. The user receives a large amount of signals which are very hard to interpret and which disturb the orientation of the blind person.

The object of the present invention is hence to provide a device to aid the orientation of blind and partially sighted people, by means of which device the head and breast area of the blind person is protectable without supplying unnecessary signals.

According to the invention, this object is achieved by a device comprising a cane, and further comprising measuring means comprising laser source means generating laser beams and laser light detecting means responding to laser light from said laser source means, said laser source means and said laser light detecting means being arranged to define a planar detection area in a detection plane comprising said cane, and indicating means for indicating the presence and the absence of an object in said planar detection area by a first and a second information, respectively.

The invention is based on the realization that the use of a device to aid the orientation of blind people is acceptable to the blind person only if the information signals concerning an obstacle can be interpreted without further considerations. Most of the blind persons are used to the long cane and even trained in use of such a long cane.

The device according to the present invention does not replace the long cane but is a combination of a long cane and an additional device comprising measuring means and indicating means. The operation of the additional device is such that it "simulates" the use of the long cane. This is effected in that the additional device only detects a determined area ("planar detection area") in a determined plane ("detection plane"). This plane is selected such that it comprises the long cane When the blind person moves the long cane in usual manner laterally to the left and to the right in order to scan the ground with the tip of the long cane, then the space above the long cane is detected by the additional device in such a manner that only a two-dimensional area above and in the prolongation of the long cane is detected. The additional device indicates the presence of an object in this planar area by providing a first information as well as the absence of an object in this planar detection area by providing a second information. The first information can, for example, be constituted by the presence of a particular (acoustic or tactile) signal and the second information can be constituted by the absence of a particular (acoustic or tactile) signal, or vice versa. The effect of this scanning is similar to the effect of scanning this space by the long cane itself, that means if the blind person could move the long cane to the left and to the right and simultaneously move it up and down. (Such a simultaneous movement of the long cane is, of course, not possible.) By this functional similarity with the function of the long cane itself, the device according to the invention does not require any training.

The principle of the measuring means used in the present invention for detecting objects in the planar detection area could be any known contactless operating principle used for measuring distances, for example the principle of time of flight measurement, the principle of triangulation measurement or the principle of phase modulation measurement. Such principle are known per se and therefore not described in detail herein.

In a preferred embodiment of the invention the measuring means operate according the principle of time of flight measurement of laser pulses. In this embodiment the laser source means are formed by laser pulse generating means for generating laser pulses. The laser light detecting means are formed by photodetector means responding to the laser pulses generated be the laser pulse generating means and reflected by an object in the planar detection area. Furthermore, signal processing means are provided. These signal processing means determine the duration between generating or sending a laser pulse by the laser pulse generating means and detecting this laser pulse by the photodetector means in relation to a predetermined duration. The laser pulse generating means can comprise one single laser source or several laser sources as well as the photodetector means can comprise one single photodetector or several photodetectors.

One possibility to arrange the measuring means to define a planar detection area exclusively in the selected detection plane can be achieved by generating several laser beams which all are located side by side in this detection plane. The number of laser beams and the closeness will then depend on the desired accuracy of detection.

A further possibility to arrange the measuring means to define a planar detection area exclusively in the selected detection plane can be achieved in that the generated laser beams are deflected by beam deflection means such that the beams are deflected in the planar detection area. Such beam deflection means can be means which either changes the direction of a beam or which deflects the beam such that the divergence of the beam is varied, for example increased in one direction or decreased in another direction to fan out the hewn. These beam deflection means can comprise, for example, an oscillating mirror which periodically deflects laser beams, for example, from one single laser source such that the two-dimensional detection area is scanned by the deflected laser beam. The beam deflection means can also comprise other beam deflection components as, for example, a prism. As mentioned above, the beam deflection means can be Laser beam divergence influencing means by which the divergence of the laser beams generated by said laser source means is increased two-dimensionally, that means in the detection plane, or decreased in a plane perpendicular to the detection plane. Such laser beam influencing means are known and can, for example, comprise a lens system having cylindrical lenses. Such beam divergence influencing means effect the laser beam to fan out in one plane and to cover an area, the extension of which depending on the extension of the angle of divergence of the beam. By using such beam divergence influencing means the planar detection area can be covered by one single laser beam having increased divergence, instead of several individual laser beams. Furthermore, this ensures that the entire planar detection area is simultaneously covered by laser radiation.

Advantageously, the device comprises limiting means for restricting the planar detection area such that the planar detection area is defined by determined limits. These limit can be defined as a function of the length of the long cane, of the extension of the long cane and of the height of the blind person using the device. Limit varying means can be provided for varying these limits of the planar detection area. These limit varying means can be used in order to individually adapt the desired planar detection area to individually different heights or individually different desires concerning the extension of the planar detection area At least one of the limits of the planar detection area can be determined by fixed or variable beam limiting means for limiting the laser beams. Such beam limiting means can, for example, be beam divergence limiting means such as filters, stop means, diaphragms or lenses, for example a cylindrical lens. The limits can be varied, for example, by replacing the lens system by another lens system having other properties with respect to the achieved beam divergence.

Furthermore, at least one of the limits of the planar detection area can be determined by time range means for defining a fixed or variable time range for detecting the laser pulses by the photodetector means. The time range can be varied by varying the time constant of a RC-network using, for example, a potentiometer. This time range can be triggered by the laser pulse generated by the laser pulse generating means. If the duration between generating the laser pulse and detecting the laser pulse is shorter than this time constant, then the object reflecting the laser pulse is located within this limit of the planar detection area. If, however, the duration between generating die laser pulse and detecting the laser pulse is longer than this time constant, then the object reflecting the laser pulse is located beyond this limit of the planar detection area.

If the long cane and the additional device is rotated or inclined, then the detection plane of the planar detection area is inclined relative to the vertical plane. This can be done on purpose in order to scan objects located laterally from the long cane. However, this tilting can be done by mistake and the blind person still thinks that the detection plane of planar detection area is vertical. In order to avoid this, inclination sensor means can be provided for determining the inclination of the detection plane of the planar detection area relative to a vertical plane. These inclination sensor means can be arranged to define a threshold angle and to generate a sensor signal when the detection plane of the planar detection area is inclined by more than this threshold angle relative to a vertical plane. This signal can be a warning signal generated by inclination indication means in the form, for example, of a tone generator indicating to the blind person that the detection plane is not aligned with the vertical plane. The amount of the inclination triggering the warning signal is determined by the threshold angle. It could be useful to define a time period between exceeding the threshold angle and generating the warning signal such that, for example, no warning signal is generated when the detection plane is inclined for only a short time in order to scan objects located laterally from the long cane. The signal generated by the inclination sensor means can also be a control signal for controlling the additional device to rotate the detection plane into the vertical plane or for turning off the laser source means.

However, the inclination indicating means can also be represented by a perceptible feature provided on the long cane or on the additional device. This perceptible feature can be an asymmetric handle of the long cane. In this case, the blind person knows in which direction the detection plane is pointing just by holding this handle in his hand.

The measuring means, the indicating and/or the inclination sensor means can be provided on the long cane in different manner. For example, they can be accommodated in a common housing or in individual housings. This or these housings can be integral with the long cane, for example be an integral part of the handle. However, the hosing or housings can also be attachable to the long cane by means of attachment means (for example screws or the like). In this way it is possible to provide an already existing long cane with the additional device defined herein.

Further objects and features of the invention will be apparent to a person skilled in the art from the following specification of a preferred embodiment when read in conjunction with the appended claims.

BRIEF DESCRIPTION OF THE DRAWING

The invention and its mode of operation will be more clearly understood from the following detailed description when read with the appended drawing in which.

Throughout the drawings, the same elements when shown in more than one figure are designated by the same reference numerals.

DESCRIPTION OF THE PREFERRED EMBODIMENT

Figure 1:
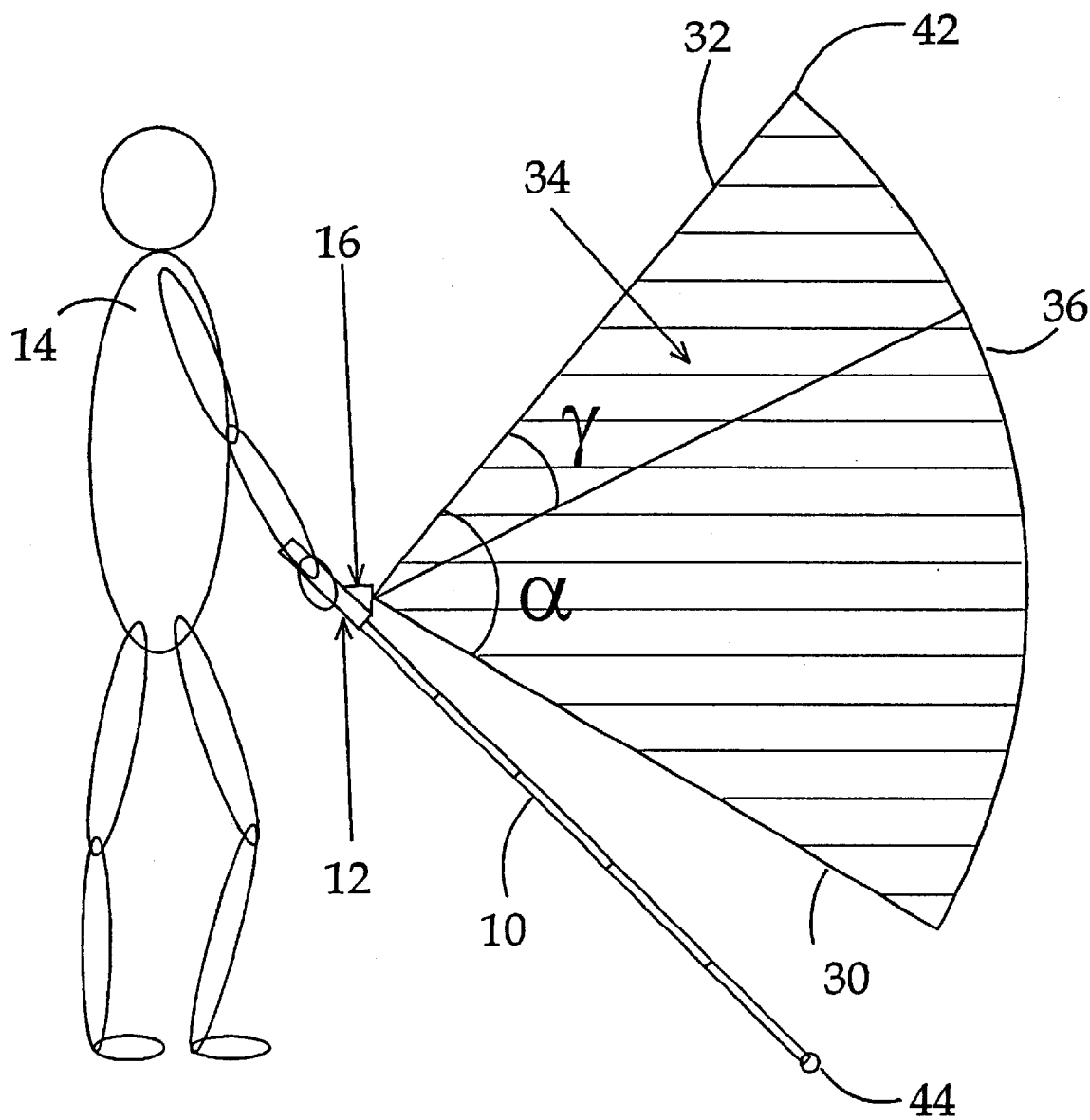
FIG. 1 is a schematic illustration and shows an embodiment of a device to aid the orientation of blind people, the device having a long cane and an additional device for detecting a planar detection area above the long cane.

Referring now to FIG. 1, there is shown a long cane 10 having a handle 12. A blind person 14 holds the handle 12 in his hand. An additional device 16 is attached to the long cane 10 on or close to the handle 12 by means of screws or the like. The additional device 16 is shown schematically in FIG. 2.

Figure 2:
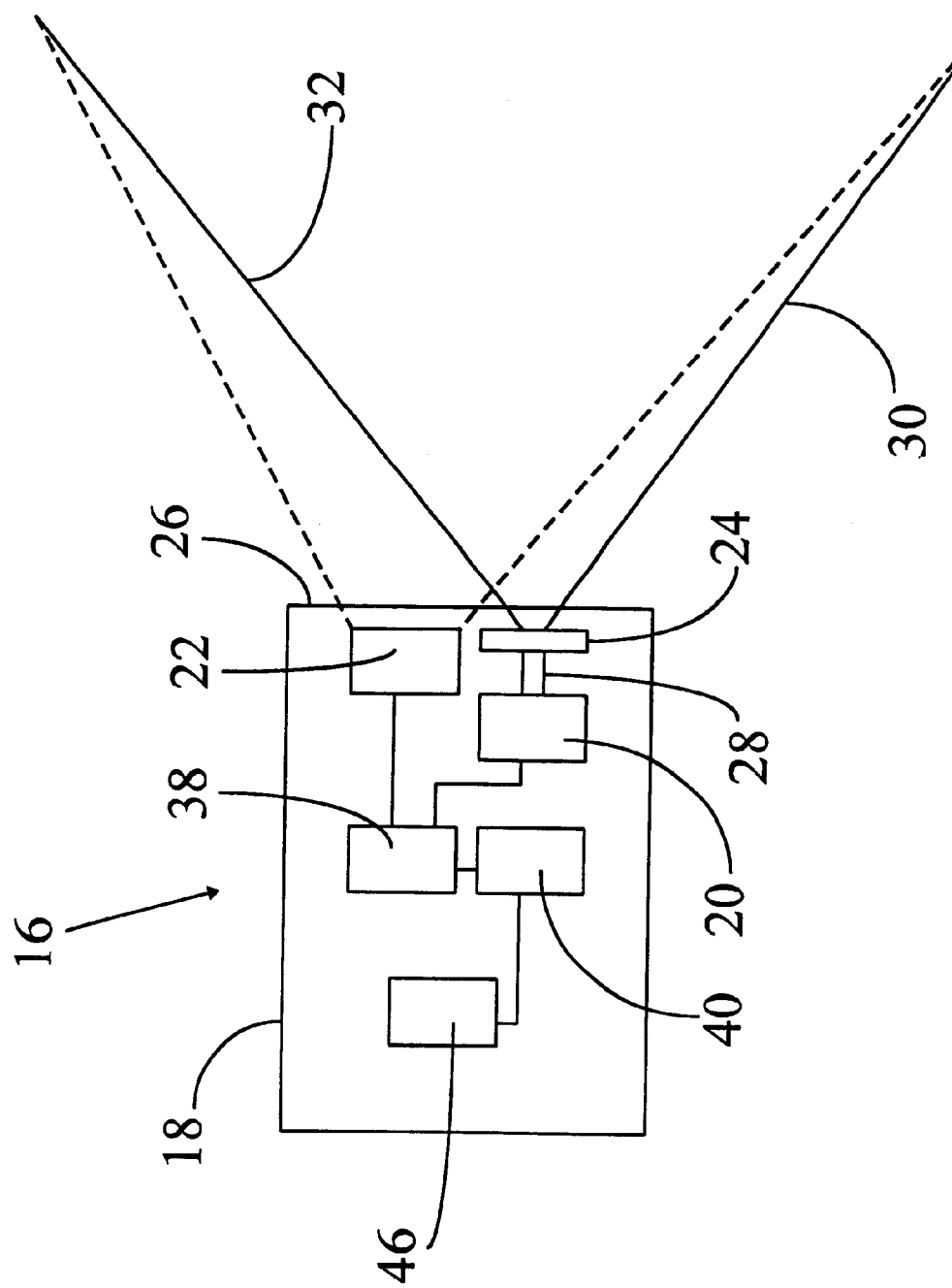
FIG. 2 is a schematic block illustration and shows the additional device of FIG. 1.

With reference to FIG. 2, there is shown a housing 18 having a transparent front wall 26. Measuring means in the form of a laser measuring system is accommodated in the housing 18. The laser measuring system comprises a transmitter unit having laser source means in the form of a laser diode 20 generating a laser beam 28. The laser measuring system firer comprises a receiver unit having laser light detecting means in the form of a photodiode 22 which responds to reflected or scattered laser radiation generated by the laser diode 20. This laser measuring system operates according to the principle of time of flight measurement of laser pulses for determining distances. Such a time of flight measurement is based on determining the period of time between the time of generating a short laser pulse by the laser diode 20 and the time of detecting this laser pulse by the photodiode 22 after it has been reflected by an object and relating this period of time to the distance between the laser measuring system and the object. This principle is known per se and therefore not described in detail herein.

Laser beam deflection means in the form of a lens system 24 comprising a cylindrical lens is arranged in front of the laser diode 20. This lens system 24 increases the divergence of the laser beam 28 generated by the laser diode 20. This divergence is increased two-dimensionally, that means that the laser beam, after passing through the lens system 24, defines a planar area ("planar detection area") in one single plane ("detection plane"). The increased divergence of die laser beam is illustrated by a first and a second boundary ray 30 and 32, respectively, defining an angle α. This planar detection area is designated by reference numeral 34 in FIG. 1. The corresponding detection plane is the same as the paper plane of FIGS. 1 and 2. The planar detection area 34 is hatched in FIG. 1 and forms a sector of a circle. The planar detection area 34 is defined by limits, namely by the first boundary ray 30 as first limit, the second boundary ray 32 as second limit and an arc of a circle 36 as third limit.

The receiver unit provided with the photodiode 22 is arranged to detect laser pulses generated by the laser diode 20 and reflected or scattered by an object located in the planar detection area 34. This is indicated by broken lines in FIG. 2 which, for better clarity, are slightly offset with respect to the boundary rays 30 and 32.

Reference numeral 38 designates signal processing means connected to the photodiode 22, to the laser diode 20 and to signal generating means in the form of a tone generator 40. The signal processing means 38 are arranged to activate the tone generator 40 to generate a signal in the form of a tone when the receiver unit detects an object in the detection area 34.

In this embodiment, the detection area 34 is defined by the design of the laser beam divergence influencing means (the lens system 24) in combination with the beam direction of the laser beam 28 generated by the laser diode 20 and by the design of the receiver unit, particularly of the signal processing means 38 as part of the receiver unit.

The laser beam divergence influencing means, here in the form of the lens system 24, determines the angle a of the sector of a circle illustrated in FIG. 2. The position of this sector of a circle relative to the long cane 10 can be defined by the alignment of the laser diode 20 or by the design of the beam divergence influencing means. A lens system 24 providing an angle α of about 80° has been chosen as beam divergence influencing means in this embodiment. However, it is possible to chose the beam divergence influencing means to provide any suitable angle, for example an angle γ of about 30°. By suitable design of the photodiode 20 and the leas system 24, the position of the sector of a circle is chosen in this embodiment such that the uppermost point 42 of the detection area 34 is located about 2 m above the ground and vertically above the point 44 of the long cane when the long cane 10 is used in usual manner, that means that it points to the ground in front of the blind person 14. In this way nearly the total area between the long cane 10 and the height of the blind person 14 is covered by the detection area 34.

In the illustrated embodiment, the position of the third limit of the detection area 34, namely the position of the arc of a circle 36, is defined by the design of the signal processing means 38. This is achieved in that the signal processing means are designed to determine whether the laser pulse detected by the photodiode 22 is reflected or scattered by an object from a distance smaller or greater than the distance between the arc of the circle 36 and the photodiode 22. This distance is preferably about the same as the length of the long cane 10. This can be achieved by designing the signal processing means 36 such that a time range is defined. Then the signal processing means 38 activates the tone generator 40 only if a defined reflected or scattered laser pulse is detected by the photodiode 22 within this time range, that means if the time of flight of this laser pulse from the laser diode 20 to the photodiode 22 is smaller than the duration of this time range.

Figure 3:
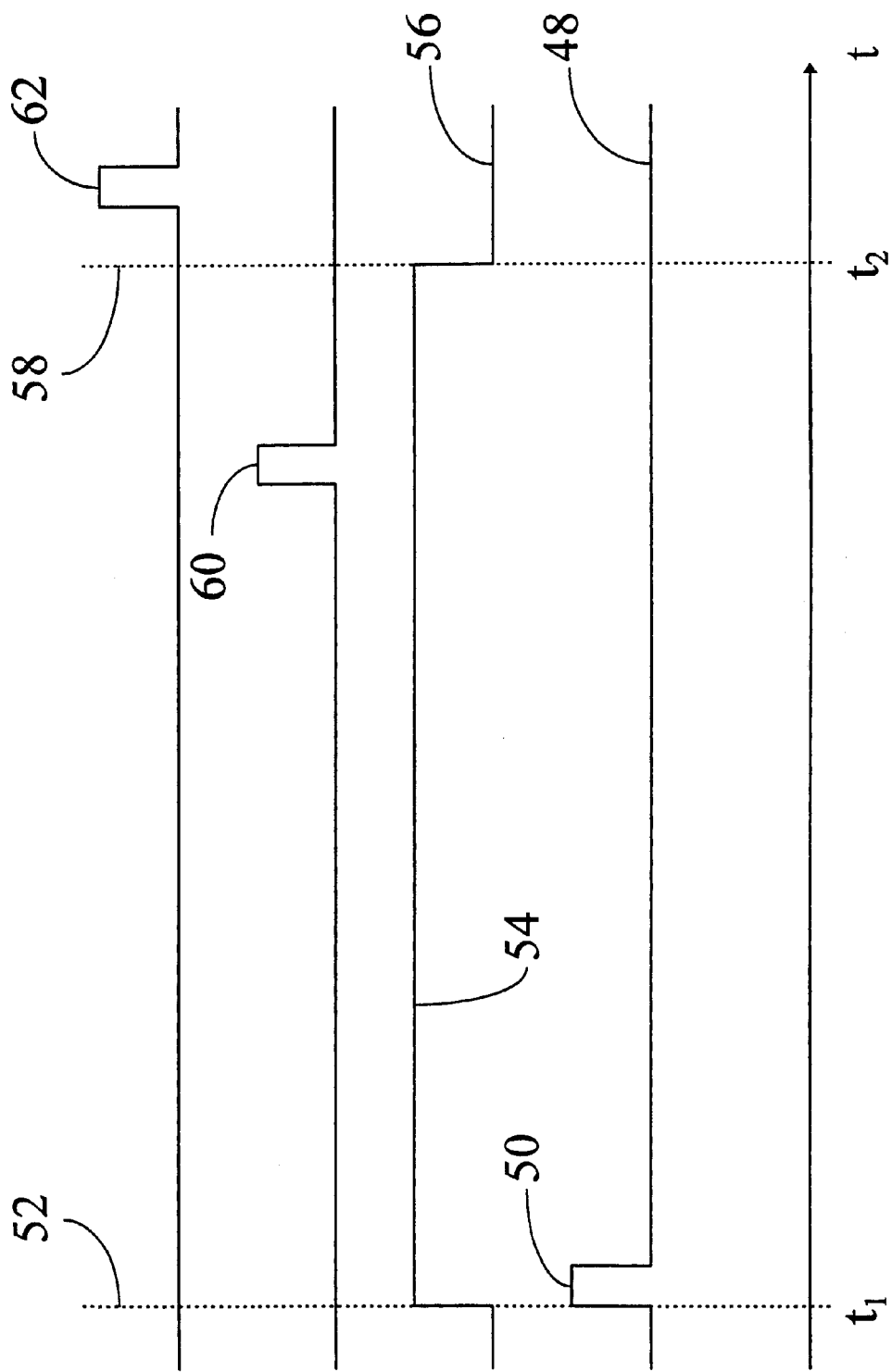
FIG. 3 shows the signal curve of a time constant for determining a limit of the planar detection area of the device of FIGS. 1 and 2.

Such a time range for determining the third limit 36 of the detection area 34 is illustrated in FIG. 3 in a time-dependency diagram. A pulse laser module generates a monitor signal, the signal curve of which is designated by reference numeral 48. The pulse laser module generates this monitor signal when a laser pulse is generated by the laser diode 20. This is assumed to be at the time to. This is illustrated in FIG. 3 by a monitor signal pulse 50 and a dotted line 52. This monitor signal pulse 50 activates a signal delay circuit of the signal processing means 38. The signal delay circuit generates a delay signal 54, the signal course of which is designated by reference numeral 56. The delay signal 54 is assumed to end at the time $t_2$. This is indicated in FIG. 3 by a dotted line 58. The duration $t_1-t_2$ of the delay signal 54 can, for example, be defined by the time constant of a time function element, for example a RC-module. This time constant and, thus, the duration $t_1-t_2$ can be variable by means of, for example, a potentiometer. The delay signal 54 is applied to a comparator. The detector signal generated by the photodiode 22 when detecting a laser pulse is likewise applied to this comparator. The comparator compares the delay signal 54 with this detector signal and determines by its output, whether the detector signal is appearing during the delay signal 54 is applied or not. If the detector signal is triggered by a laser pulse reflected or scattered by an object within the limit 36, then this detector signal appears within the duration $t_1-t_2$ of the delay signal 54. Such a detector signal is designated by reference numeral 60 in FIG. 3. If the detector signal is triggered by a laser pulse reflected or scattered by an object beyond the limit 36, then this detector signal does not appears within the duration $t_1-t_2$ of the delay signal 54. Such a detector signal is designated by reference numeral 62 in FIG. 3.

As mentioned above, the limits 30, 32 and 36 of the detection area 34 are variable relative to the long cane 10 in order to set these limits according to individual desires. The variation of the limits is effected, on one hand, by varying the duration of the delay signal 54 and, thus, varying the distance between the laser measuring system and the arc of a circle 36, and, on the other hand, by varying the divergence angle α (FIG. 1) of the laser beam and varying the position of the illustrated sector of a circle relative to the long cane 10. This can be effected, for example, by a variable diaphragm determining the divergence of the laser beam. However, the variation of the divergence angle α can also be effected by replacing the lens system 24 by another lens system having other properties. In FIG. 1 an alternative divergence angle γ of about 30° is illustrated resulting from the use of another lens system with the property of diverging the laser beam in this way.

Furthermore, inclination sensor means 46 are accommodated in the hosing 18 of the additional device 16. These inclination sensor means 46 monitors the position of the long cane 10 and of the detection plane of the planar detection area 34. Such inclination sensor means 46 are known per se and therefore not described in detail herein. By means of a control circuit a warning signal is generated, either by the tone generator 40 or by other signal generating means, when the detection plane of the planar detection area 34 is inclined by more than a determined threshold angle of, for example, 15° relative to a vertical plane.

A further measure in order to determine or to avoid an inclination of the detection plane of the planar detection area 34 consist in that the handle 12 of the long cane 10 is designed asymmetrically. Thus, in this case, the blind person can, just by holding this asymmetric handle in his hand, immediately recognize the amount of inclination of the detection plane.

Furthermore, energy supply means (not shown), for example a battery, are provided in the housing 18 in order to supply electrical current to the current-consuming components of the additional device 16.

Preferably, in order to achieve a suitable distribution of weights, the additional device 16 is provided on or in the handle 16. In this embodiment, the entire additional device 16 is an integral part of the handle 12 of the long cane.

We claim:
1. A device having a cane (10) to aid the orientation of blind people, comprising:
   a. detection means (20, 22, 38) which, by emitting and receiving laser beams, detect objects in a two-dimensional detection area located in a detection plane containing the cane (10) and comprise:
      i. beam deflection means (24) for deflecting the emitted laser beams (28) in this detection area, and
      ii. receiving means (22) which respond to the emitted laser beams after they have been reflected or scattered by an object located in this detection area,
   b. indicating means (40) which
      i. indicate the presence of an object in the thus generated two dimensional detection area (34) by a first information, and
      ii. indicate the absence of an object in the thus generated two-dimensional detection area (34) by a second information.
2. Device as set forth in claim 1, characterized in that the detection means are adapted for time of flight measurement of laser beams and comprise
   a. laser beam generating means (20) for generating laser pulses,
   b. photodetector means (22) responding to these laser pulses, and
   c. signal processing means (38) arranged to determine the duration between emitting a laser pulse by the laser pulse generating means (20) and detecting the laser pulse by the photodetector means (22).
3. Device as set forth in claim 2, characterized in that the first and/or the second information is represented by acoustic and/or tactile signals.
4. Device as set forth in claim 1, characterized in that the first and/or the second information is represented by acoustic and/or tactile signals.
5. Device as set forth in claim 1, characterized in that the beam deflection means comprise beam divergence increasing means (24) for two-dimensionally increasing the divergence of the emitted laser beams (28).
6. Device as set forth in claim 5, characterized in that the beam divergence increasing means (24) comprise a cylindrical lens (24).
7. Device as set forth in claim 5, characterized in that the detection means (20, 22, 38) are designed such that the detection area (34) in the detection plane is defined by limits (30, 32, 36).
8. Device as set forth in claim 7, characterized in that the limits (30, 32, 36) of the detection area (34) are adjustable.
9. Device as set forth in claim 8, characterized in that at least one of the limits (30, 32, 36) is defined by fixed or variable beam limiting means (24) for limiting the emitted laser beams.
10. Device as set forth in claim 9, characterized in that at least one of the limits (36) is defined by the signal processing means (38) with a fixed or variable electronic time window (54) for detecting the laser pulse by the photodetector means (22).
11. Device as set forth in claim 7, characterized in that at least one of the limits (36) is defined by the signal processing means (38) with a fixed or variable electronic time window (54) for detecting the laser pulse by the photodetector means (22).
12. Device as set forth in claim 1, characterized in that the detection means (20, 22, 38) are designed such that the detection area (34) in the detection plane is defined by limits (30, 32, 36).
13. Device as set forth in claim 12, characterized in that the limits (30, 32, 36) of the detection area (34) are adjustable.
14. Device as set forth in claim 13, characterized in that at least one of the limits (30, 32, 36) is defined by fixed or variable beam limiting means (24) for limiting the emitted laser beams.
15. Device as set forth in claim 14, characterized in that at least one of the limits (36) is defined by the signal processing means (38) with a fixed or variable electronic time window (54) for detecting the laser pulse by the photodetector means (22).
16. Device as set forth in claim 1, characterized by inclination sensor means (46) which generate a signal when the detection plane containing the detection area (34) is inclined by more than a predetermined threshold angle relative to the vertical plane.
17. Device as set forth in claim 1, characterized by inclination indicating means (40) for indicating an inclination of the detection plane containing the detection area (34) relative to the vertical plane.
18. Device as set forth in claim 17, characterized in that the inclination indicating means comprise a perceptible feature provided on the cane (10).

19. Device as set forth in claim 16, characterized in that the detection means (20, 22, 38), the indicating means (40) and/or the inclination sensor means (46) are accommodated in a common housing (18) or in separate housings which are integrated in the cane (10) or adapted to be attached to the cane (10) by means of attachment means.

20. Device as set forth in claim 1, characterized in that the laser beam generating means comprise one single laser source (20) and/or the photodetector means comprise one single photodetector (22).

* * * * *